(12) United States Patent
Hyogo et al.

(10) Patent No.: US 6,453,184 B1
(45) Date of Patent: Sep. 17, 2002

(54) DEVICE FOR MEASURING LIGHT ABSORPTION MATERIALS IN BLOOD

(75) Inventors: Mitsushi Hyogo; Teiji Ukawa; Hideo Ozawa, all of Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 79 days.

(21) Appl. No.: 09/661,199

(22) Filed: Sep. 13, 2000

(30) Foreign Application Priority Data

Sep. 13, 1999 (JP) .......................................... 11-258905

(51) Int. Cl.$^7$ ................................................. A61B 5/00
(52) U.S. Cl. ........................ 600/323; 600/330; 600/336
(58) Field of Search ................................. 600/309, 310, 600/322, 324, 330, 336; 356/39–42

(56) References Cited

U.S. PATENT DOCUMENTS 4,714,341 A * 12/1987 Hamaguri et al. ............. 356/41
5,137,023 A * 8/1992 Mendelson et al. ......... 600/316
6,067,462 A * 5/2000 Diab et al. ................... 600/310

FOREIGN PATENT DOCUMENTS

| JP | 6-22943 | 2/1994 | ............ A61B/5/14 |
| JP | 11-155841 | 6/1999 | ............ A61B/5/14 |

* cited by examiner

Primary Examiner—Eric F. Winakur
Assistant Examiner—Matthew J. Kremer
(74) Attorney, Agent, or Firm—Sughrue Mion, PLLC

(57) ABSTRACT

A red light and an infrared light which are emitted from a light emitting portion 2 are transmitted through a fingertip 4 of a subject and are converted into electric signals by a light receiving portion 3. The respective signals are separated and amplified and are then sent to a CPU 8. In the CPU 8, the input signals are divided into D.C. components DC1 and DC2 and A.C. components AC1 and AC2, changes $\Delta A1 = (AC/DC)1$ and $\Delta A2 = (AC/DC)2$ in an absorbance are calculated, high frequency components thereof are extracted, a mutual ratio $\Psi$ is calculated, and a noise removing waveform is calculated based thereon. Based on the noise removing waveform, a pulse wave is detected, a pulse rate is calculated, a display wave form is calculated and an oxygen saturation is calculated. These are displayed through a display unit 11.

14 Claims, 6 Drawing Sheets

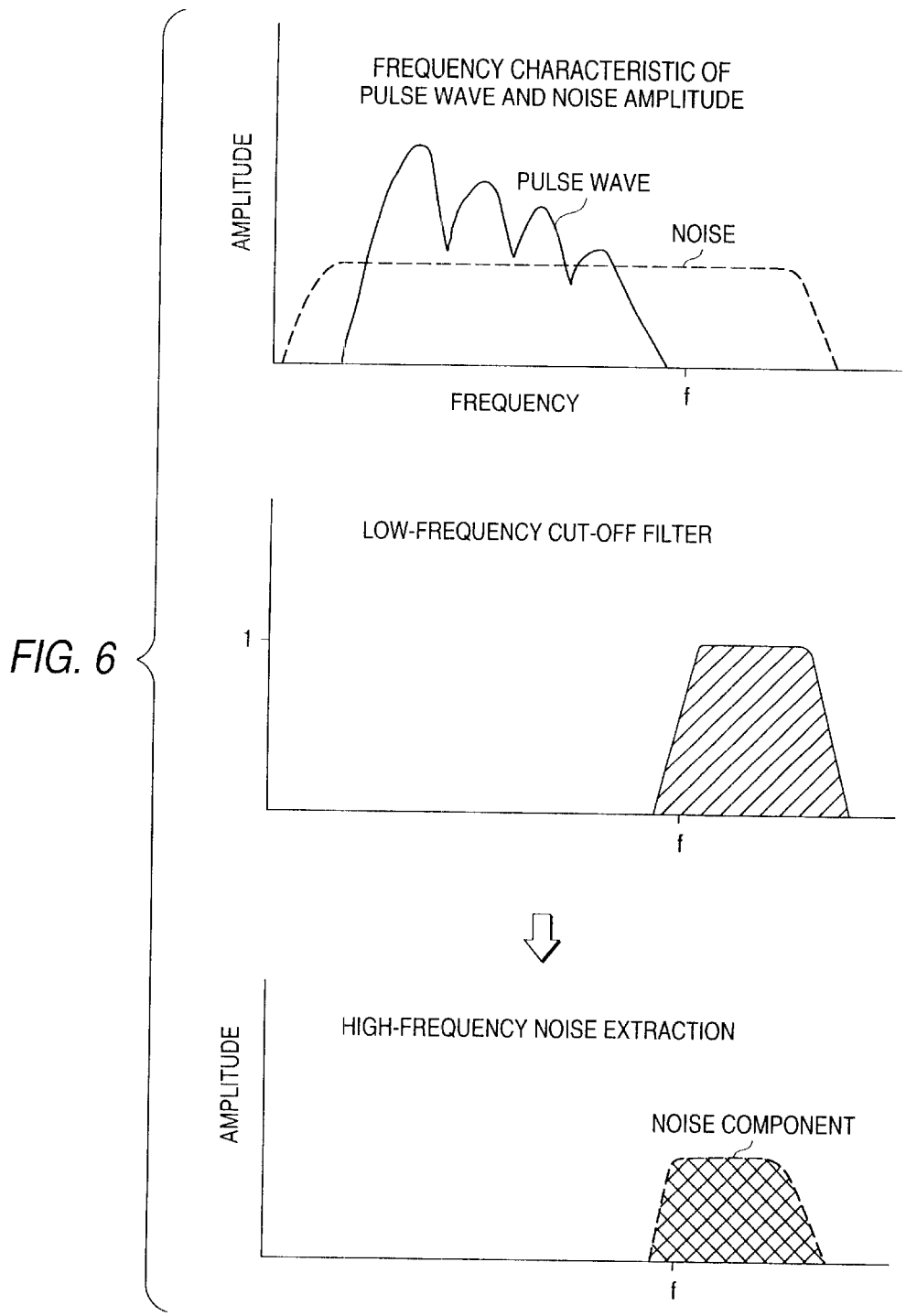

DEVICE FOR MEASURING LIGHT ABSORPTION MATERIALS IN BLOOD

BACKGROUND OF INVENTION

1. Field of invention

The present invention relates to a device for measuring a light absorption material in blood which serves to emit a light onto a living tissue, to process a signal based on an intensity of a transmitted light or a reflected light, thereby detecting information about the light absorption material in blood such as an oxygen saturation.

2. Related art

In the device of this kind, in the case in which a noise made by a body movement or a probe slip-off is mixed into a signal based on the intensity of the transmitted light or the reflected light, a signal measured previously is subjected to an averaging process. Based thereon, for example, an oxygen saturation or a pulse rate is calculated.

Furthermore, in the case in which a large noise is made or a noise is mixed for a long period of time, an oxygen saturation and a pulse rate which are obtained before the mixture of the noise are retained and displayed.

However, if a measured value obtained before the mixture of the noise is used, a change in the oxygen saturation or the pulse rate cannot be known at the present time. Consequently, there is a possibility that a critical condition might be missed.

SUMMARY OF INVENTION

The present invention has been made to avoid such a situation and has an object to remove a noise in a signal processing based on an intensity of a transmitted light or a reflected light for a living tissue, thereby accurately obtaining information about a light absorption material in blood.

A first aspect of the invention is directed to a device for measuring a light absorption material in blood comprising light emitting means for emitting lights having a plurality of different wavelengths onto a living tissue, light receiving means for receiving a transmitted light or a reflected light for the living tissue from the light emitting means and for outputting a signal corresponding to an intensity thereof, D.C./A.C. detecting means for obtaining a D.C. component and an A.C. component for a signal corresponding to each wavelength which is the output signal of the light receiving means, respectively, A.C. to D.C. ratio detecting means for obtaining an A.C. to D.C. ratio signal which is a ratio of the A.C. component to the D.C. component for each wavelength calculated by the D.C./A.C. detecting means, component extracting means for extracting a component having a predetermined frequency or more for the A.C. to D.C. ratio signal having each wavelength which is obtained by the A.C. to D.C. ratio detecting means, extracted component ratio detecting means for obtaining a mutual ratio of an extracted component signal having each wavelength which is extracted by the component extracting means, and means for detecting information about a light absorption material in blood based on the ratio detected by the extracted component ratio detecting means.

Consequently, the ratio detected by the extracted component ratio detecting means can be set to a ratio of wavelengths of only a noise signal. Furthermore, the ratio can be regarded as equal over the whole frequency range of the A.C. to D.C. ratio signal obtained by a measurement. Therefore, if the A.C. to D.C. ratio signal is processed by using the ratio in place of the noise signal, the processing can be simplified.

A second aspect of the invention is directed to the device for measuring a light absorption material in blood according to the first aspect of the invention, wherein the information detecting means serves to detect an ideal signal assumed when the A.C. to D.C. ratio signal has no noise based on a predetermined relationship among the ratio detected by the extracted component ratio detecting means, the A.C. to D.C. ratio signal detected by the A.C. to D.C. ratio detecting means and the ideal signal, and to detect the information about the light absorption material in blood.

Consequently, the ideal signal is obtained without a noise signal. Therefore, information about a desirable light absorption material in blood can be obtained with high precision.

A third aspect of the invention is directed to a device for measuring a light absorption material in blood, comprising light emitting means for emitting lights having a plurality of different wavelengths onto a living tissue, light receiving means for receiving a transmitted light or a reflected light for the living tissue from the light emitting means and for outputting a signal corresponding to an intensity thereof, D.C./A.C. detecting means for obtaining a D.C. component and an A.C. component for a signal corresponding to each wavelength which is the output signal of the light receiving means, A.C. to D.C. ratio detecting means for obtaining an A.C. to D.C. ratio signal which is a ratio of the A.C. component to the D.C. component for each wavelength calculated by the D.C./A.C. detecting means, noise condition deciding means for deciding at least whether a high frequency component of a noise included in the A.C. to D.C. ratio signal is large, and a plurality of signal processing means provided corresponding to a result of the decision of the noise condition deciding means respectively for processing the A.C. to D.C. ratio signal having each wavelength which is obtained by the A.C. to D.C. ratio detecting means, thereby detecting information about a light absorption material in blood, the signal processing means provided corresponding to a case in which the noise condition deciding means decides that the high frequency component of the noise is large, including component extracting means for extracting a component having a predetermined frequency or more for the A.C. to D.C. ratio signal having each wavelength which is obtained by the A.C. to D.C. ratio detecting means, extracted component ratio detecting means for obtaining a mutual ratio of an extracted component signal having each wavelength which is extracted by the component extracting means, and means for detecting information about a light absorption material in blood based on the ratio detected by the extracted component ratio detecting means.

Consequently, different processings are carried out depending on the noise condition. Therefore, a result of a measurement can be obtained with higher precision. In particular, in the case in which. the high frequency component of the noise is large, the same function can be obtained because of the same structure according to the first aspect of the invention.

A fourth aspect of the invention is directed to the device for measuring a light absorption material in blood according to the third aspect of the invention, wherein the information detecting means serves to detect an ideal signal assumed when the A.C. to D.C. ratio signal has no noise based on a predetermined relationship among the ratio detected by the extracted component ratio detecting means, the A.C. to D.C. ratio signal detected by the A.C. to D.C. ratio detecting means and the ideal signal, and to detect the information about the light absorption material in blood.

Since the structure is the same as that in the second aspect of the invention, the same function can be obtained.

A fifth aspect of the invention is directed to the device for measuring a light absorption material in blood according to the second or fourth aspect of the invention, further comprising pulse rate detecting means for detecting a pulse rate based on the ideal signal. Consequently, the pulse rate can also be detected in addition to the information about the light absorption material in blood.

A sixth aspect of the invention is directed to the device for measuring a light absorption material in blood according to the second or fourth aspect of the invention, further comprising display means for displaying a waveform of the ideal signal. Consequently, a pulse signal having no noise is displayed.

A seventh aspect of the invention is directed to the device for measuring a light absorption material in blood according to the first or third aspect of the invention, the predetermined frequency is a substantially pulsation frequency of living tissue.

An eighth aspect of the invention is directed to the structure in which the information about the light absorption material in blood is an oxygen saturation. Consequently, the oxygen saturation can be measured with high precision.

A ninth aspect of the invention is directed to the structure in which two wavelengths are used as the different wavelengths.

BRIEF DESCRIPTION OF DRAWINGS

FIG. 6 is a chart showing a process for extracting the high frequency component of a noise.

DETAILED DESCRIPTION OF PREFERRED EMBODIMENTS

Figure 1:
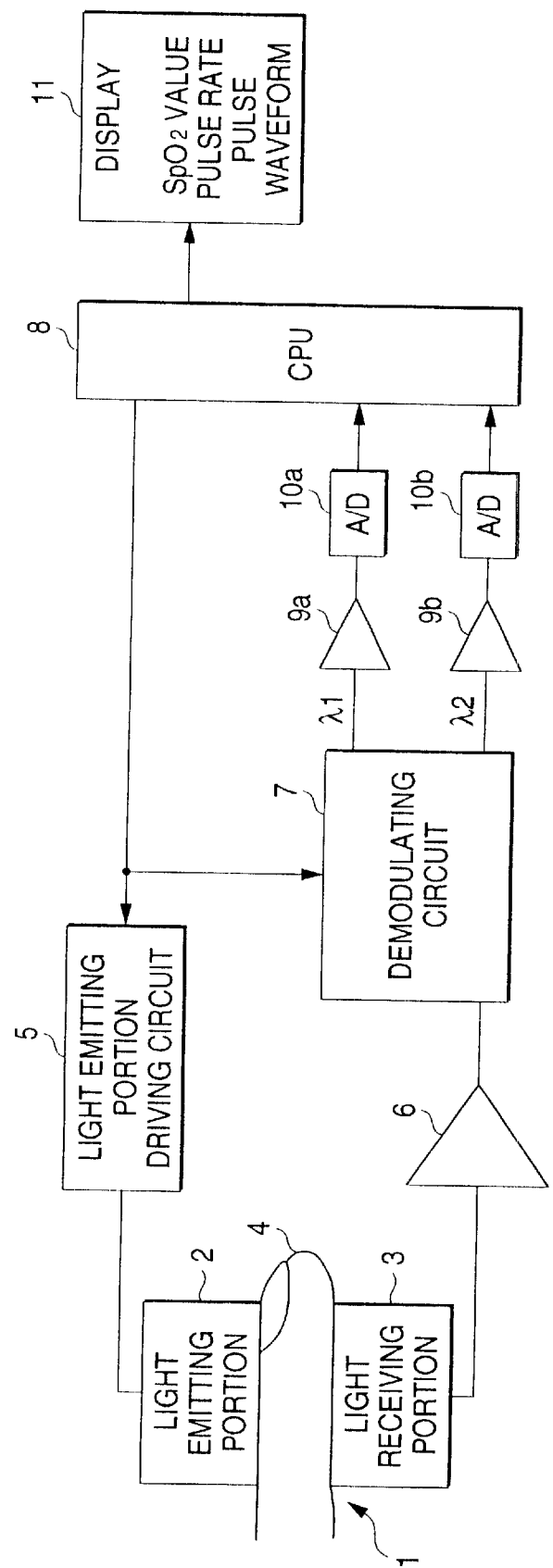
FIG. 1 is a diagram showing the whole structure of a pulse oximeter according to the invention.

Primarily, the basic principle of the invention will be described. For example, lights having two different wavelengths $\lambda 1$ and $\lambda 2$ are emitted onto a living tissue. It has been known that the relationship between an intensity of a transmitted light or a reflected light for each wavelength and changes $\Delta A1$ and $\Delta A2$ in an absorbance of the living tissue can approximate in the following manner based on the Lambert-Beer's law:

$$\Delta A1 = (AC/DC)1 \quad (1)$$

$$\Delta A2 = (AC/DC)2 \quad (2)$$

wherein AC represents an A.C. component of the intensity of the transmitted light or the reflected light, DC represents a D.C. component of the intensity of the transmitted light or the reflected light, and appended numerals 1 and 2 represent a wavelength (and so forth).

In the case in which a noise is made due to a body movement or a probe slip-off, changes $\Delta A1$ and $\Delta A2$ in an actual absorbance are expressed in the following manner:

$$\Delta A1 = (AC/DC)1 = (AC/DC)S1 + (AC/DC)N1 \quad (3)$$

$$\Delta A2 = (AC/DC)2 = (AC/DC)S2 + (AC/DC)N2 \quad (4)$$

wherein (AC/DC)S represents a change in an absorbance assumed when no noise is made and a signal (hereinafter referred to as a pulse signal) indicating a change caused by the genuine pulsation of a living tissue, and (AC/DC)N represents a signal (hereinafter referred to as a noise signal) indicating a change in an absorbance caused by the noise.

Figure 5:
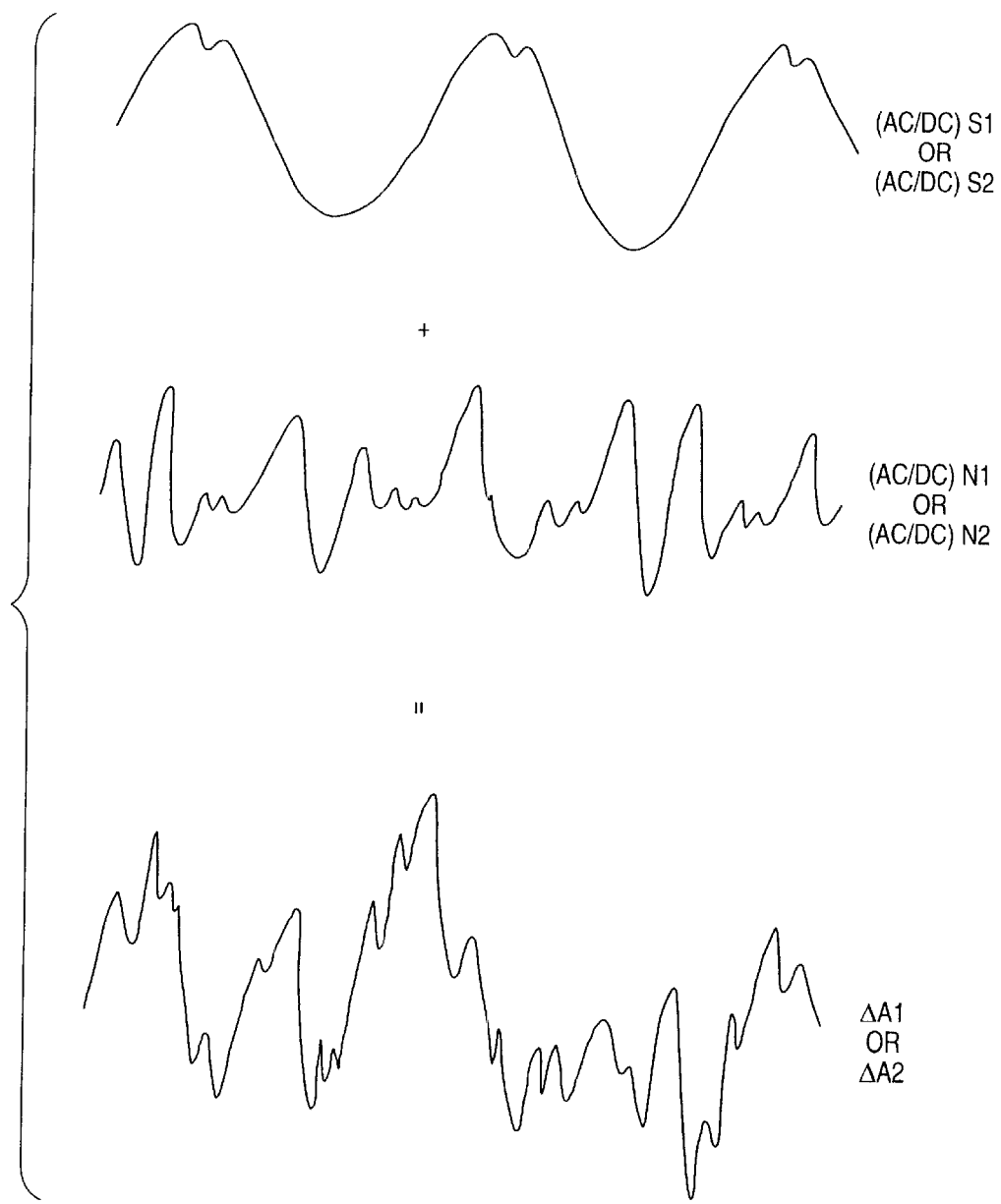
FIG. 5 is a chart showing the relationship among a measuring signal, a pulse signal and a noise signal.

FIG. 5 shows the relationship among the measuring signals $\Delta A1$ and $\Delta A2$, the pulse signals (AC/DC)S1 and (AC/DC)S2 and the noise signals (AC/DC)N1 and (AC/DC)N2.

Next, a component having a high frequency f, which is not less than a pulsation frequency of the living tissue, is extracted from the frequency components of the measuring signals $\Delta A1$ and $\Delta A2$. In this case, components $\Delta Af1$ and $\Delta Af2$ having the frequency f or more in the frequency components of the measuring signals $\Delta A1$ and $\Delta A2$ are expressed in the following equations using only a noise component based on the equations (3) and (4).

$$\Delta Af1 = (AC/DC)N1 \quad (5)$$

$$\Delta Af2 = (AC/DC)N2 \quad (6)$$

When a ratio of $\Delta Af1$ to $\Delta Af2$ is calculated, a ratio of (AC/DC)N1 to (AC/DC)N2 can be obtained. When the ratio is represented as $\Psi$, the following equation is obtained.

$$\Psi = \{(AC/DC)N2\}/\{(AC/DC)N1\} \quad (7)$$

FIG. 6 shows a process for extracting the noise signal in the high frequency range.

On the other hand, if a ratio of the pulse signals (AC/DC)S1 to (AC/DC)S2 is represented as $\Phi$, the following equation is obtained.

$$\Phi = \{(AC/DC)S2\}/\{(AC/DC)S1\} \quad (8)$$

When $\Phi$ is known, an oxygen saturation can be usually obtained.

If $\Psi$ and $\Phi$ are used, the following equation is obtained based on the equation (4).

$$\Delta A2 = (AC/DC)S2 + (AC/DC)N2 = \Phi(AC/DC)S1 + \Psi(AC/DC)N1 \quad (9)$$

While the value of $\Psi$ for a noise is obtained in the high frequency range of the measuring signal, it is considered that the noise rarely has a specific frequency and is equal over the whole frequencies. The following equations are obtained based on the equations (3) and (9).

$$\Delta A2 - \Psi \Delta A1 = (\Phi - \Psi)(AC/DC)S1 \quad (10)$$

Similarly, the following equation is obtained.

$$\Delta A2 - \Phi \Delta A1 = (\Psi - \Phi)(AC/DC)N1 \quad (11)$$

In the equation (10), the pulse signal (AC/DC)S1 is represented by the measuring signals $\Delta A2$ and $\Delta A1$. $\Psi$ can be calculated as described above. Therefore, if $\Phi$ is known, the pulse signal (AC/DC)S1 can be obtained.

In the equation (11), the noise signal (AC/DC)N1 is represented by the measuring signals $\Delta A2$ and $\Delta A1$. $\Psi$ can be calculated as described above. Therefore, if $\Phi$ is known, the noise signal (AC/DC)N1 can be obtained.

Accordingly, $\Phi$ is sequentially varied, the cross-correlation function of each of the equations (10) and (11) for each $\Phi$ is taken. $\Phi$ obtained with a correlation coefficient of zero is correct. Consequently, an oxygen saturation can be obtained.

Preferred embodiments will be described here in below. FIG. 1 shows a pulse oximeter according to an embodiment of the invention. A probe 1 comprises a light emitting portion 2 and a light receiving portion 3, there by holding a fingertip (a living tissue) 4 therebetween. The light emitting portion 2 includes two light emitting diodes for emitting a red light (wavelength λ1) and an infrared light (wavelength λ2) respectively. The light emitting portion 2 is driven by a light emitting portion driving circuit 5.

The light receiving portion 3 includes a photodiode and serves to receive the transmitted light of the fingertip and to output an electric signal corresponding to an intensity of the transmitted light. The output signal of the light receiving portion 3 is amplified by a light-receiving signal amplifying circuit 6 and is demodulated by a demodulating circuit 7. The demodulating circuit 7 divides and outputs the respective signals corresponding to the red light and the infrared light. These signals are amplified by amplifiers 9a and 9b, are converted into digital signals through analog to digital converters 10a and 10b and are sent to a CPU (Central Processing Unit) 8.

The CPU 8 serves to control the demodulating circuit 7 and the light emitting portion driving circuit 5, to process the signals sent from the analog to digital converters 10a and 10b and to output the result of the processing to a display unit 11. The CPU 8 executes a processing based on the flow chart of FIG. 2.

When a measurement is started, the CPU 8 controls the light emitting portion driving circuit 5 to alternately generate a red light and an infrared light from the light emitting portion 2. These lights are transmitted through the fingertip 4 of a subject, are converted into electric signals by the light receiving portion 3, and are then sent to the CPU 8 through the light-receiving signal amplifying circuit 6, the demodulating circuit 7, the amplifiers 9a and 9b, and the analog to digital converters 10a and 10b.

Next, the operation of the device having such a structure will be described with reference to FIG. 2. At a step 101, an input waveform is preprocessed. The input measuring signal is divided into D.C. components DC1 and DC2 and A.C. components AC1 and AC2. After the D.C. components and the A.C. components are obtained, AC1/AC2 and DC1/DC2 are calculated (step 102). Moreover, changes ΔA1=(AC/DC)1 and ΔA2=(AC/DC)2 in an actual absorbance are calculated (step 103). Furthermore, after ΔA1 and ΔA2 are obtained, a pulse wave is detected from the waveforms, a pulse rate is calculated and an oxygen saturation (SpO2) is calculated, and the results thereof are retained (step 105).

On the other hand, after ΔA1 and ΔA2 are obtained at the step 103, high frequency components thereof are extracted, Ψ is calculated and a noise removing waveform is calculated (step 104). These calculating methods have been described in the explanation of the principle. A frequency f for determining the high frequency component to be extracted may be previously stored in the CPU 8 or the CPU 8 may determine the frequency f based on the frequency characteristics of an input signal.

Next, a noise condition of the input signal is decided (step 106). Based on the result of the decision, the following three processings are carried out separately.

(1) If it is decided that a small noise is made or no noise is made at the step 106, the pulse rate and the oxygen saturation which are obtained at the step 105 are displayed through the display unit 11 (step 108).

Figure 3:
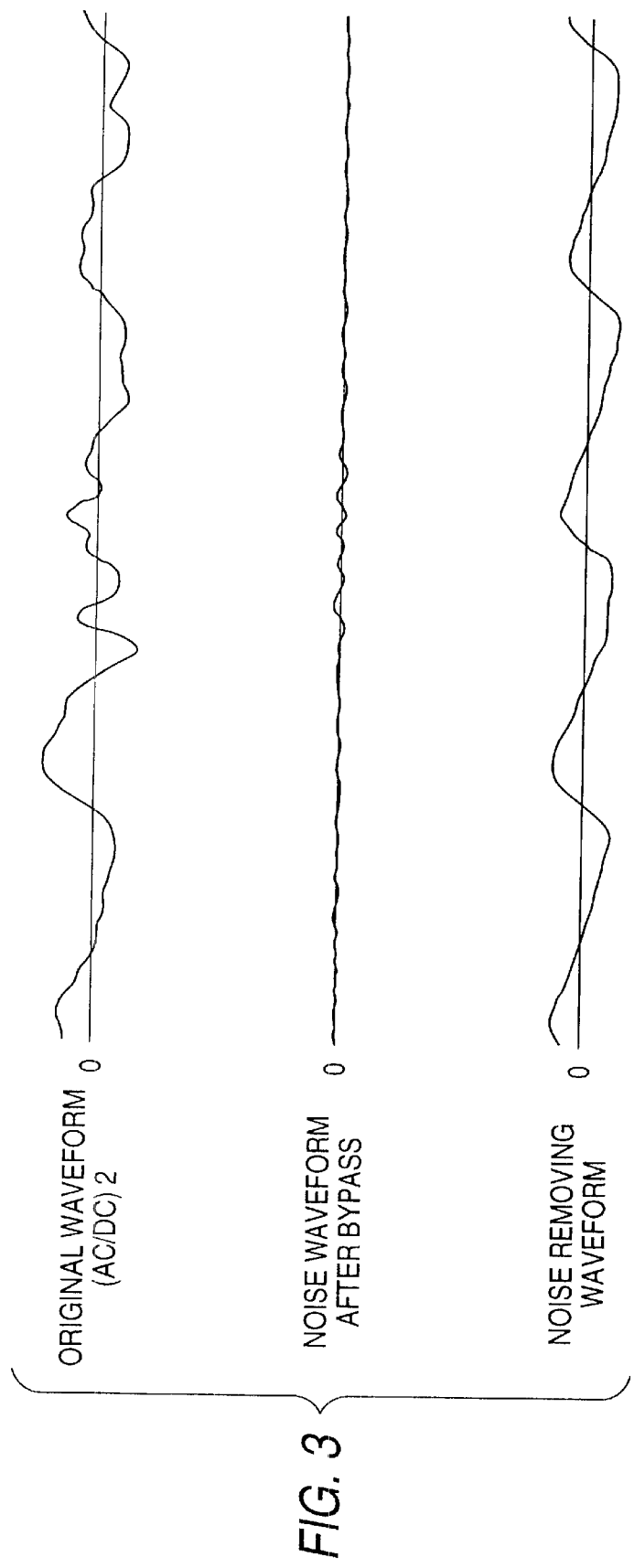
FIG. 3 is a chart showing a result of an actual measurement obtained by the device illustrated in FIG. 1.

(2) If a noise component having a frequency which is higher than a pulsation frequency of the living tissue is larger than a predetermined threshold at the step 106, a pulse wave is detected based on the noise removing waveform obtained at the step 104, a pulse rate is calculated, a display waveform is calculated and an oxygen saturation is calculated (step 107). The pulse rate, the display waveform and the oxygen saturation which are obtained at the step 107 are displayed through the display unit 11 (step 108). FIG. 3 shows an example of an original waveform (AC/DC)2 obtained by an actual measurement, a noise signal in a high frequency range which is extracted, and a pulse signal having a noise removed.

Figure 4:
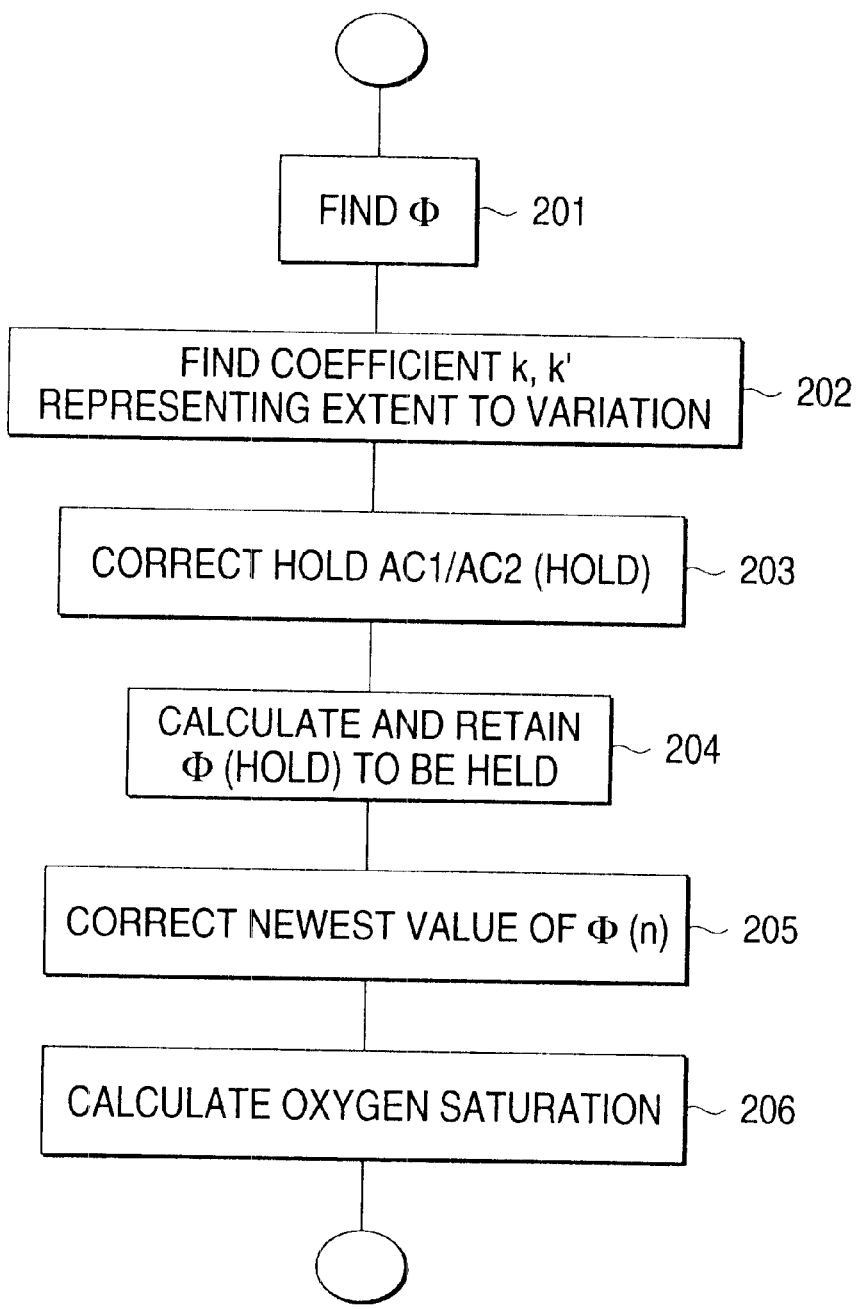
FIG. 4 is a flow chart for explaining the operation of the device shown in FIG. 1.

(3) If a noise component having a frequency which is equal or lower than the pulsation frequency of the living tissue is larger than another predetermined threshold at the step 106, a processing of calculating an oxygen saturation is carried out by using a stable signal (step 109). The processing is shown in FIG. 4. Description will be given to the processing. First of all, Φ is calculated based on the AC1/AC2 and the DC2/DC1 which are obtained at the step 102 (step 201). Φ=(AC1/AC2)×(DC2/DC1) is calculated per each one pulse. Φ for an nth pulse is represented as Φ(n).

Next, coefficients k and k' representing the extent of a variation of Φ are found (step 202). The coefficients k and k' are calculated by the following equations:

$$k(n)=a\{\Delta^2\Phi(n)+\Delta^2\Phi(n+1)+\Delta^2\Phi(n+2)\} \quad (12)$$

$$k'(n)=b\{\Delta^2\Phi(n)+\Delta^2\Phi(n+1)+\Delta^2\Phi(n+2)\} \quad (13)$$

wherein $\Delta^2\Phi(n)$ represents a secondary difference of Φ(n). The secondary difference is obtained from a primary difference $\Delta\Phi(n)$. The primary difference $\Delta\Phi(n)$ is obtained in the following equation:

$$\Delta\Phi(n)=\Phi(n)-\Phi(n-1) \quad (14)$$

and the secondary difference $\Delta^2\Phi(n)$ is obtained in the following equation:

$$\Delta^2\Phi(n)=\Delta\Phi(n)-\Delta\Phi(n-1) \quad (15)$$

wherein a and b are proper constants.

Next, it is decided that Φ has a variation. If Φ has a variation, a latest hold value (AC1/AC2(HOLD)) held during stable period is corrected and retained (step 203). (AC1/AC2(HOLD)) is corrected by the following equation. The corrected hold value is represented as (AC1/AC2(HOLD))':

$$(AC1/AC2(HOLD))'=(1-k')(ACn1/ACn2)+k'(AC1/AC2(HOLD)) \quad (16)$$

wherein ACn1 and ACn2 are the latest measured values of AC1 and AC2.

Next, Φ(HOLD) to be held is calculated and retained (step 204). The Φ(HOLD) is obtained by the following equation.

$$\Phi(HOLD)=(AC1/AC2(HOLD))'\times(ACn1/ACn2) \quad (17)$$

Subsequently, the latest value of Φ(n) is corrected (step 205). The correction is calculated based on a relationship expressed in the following equation.

$$\Phi'=(1-k)\Phi(n)+k\Phi(HOLD) \quad (18)$$

Figure 2:
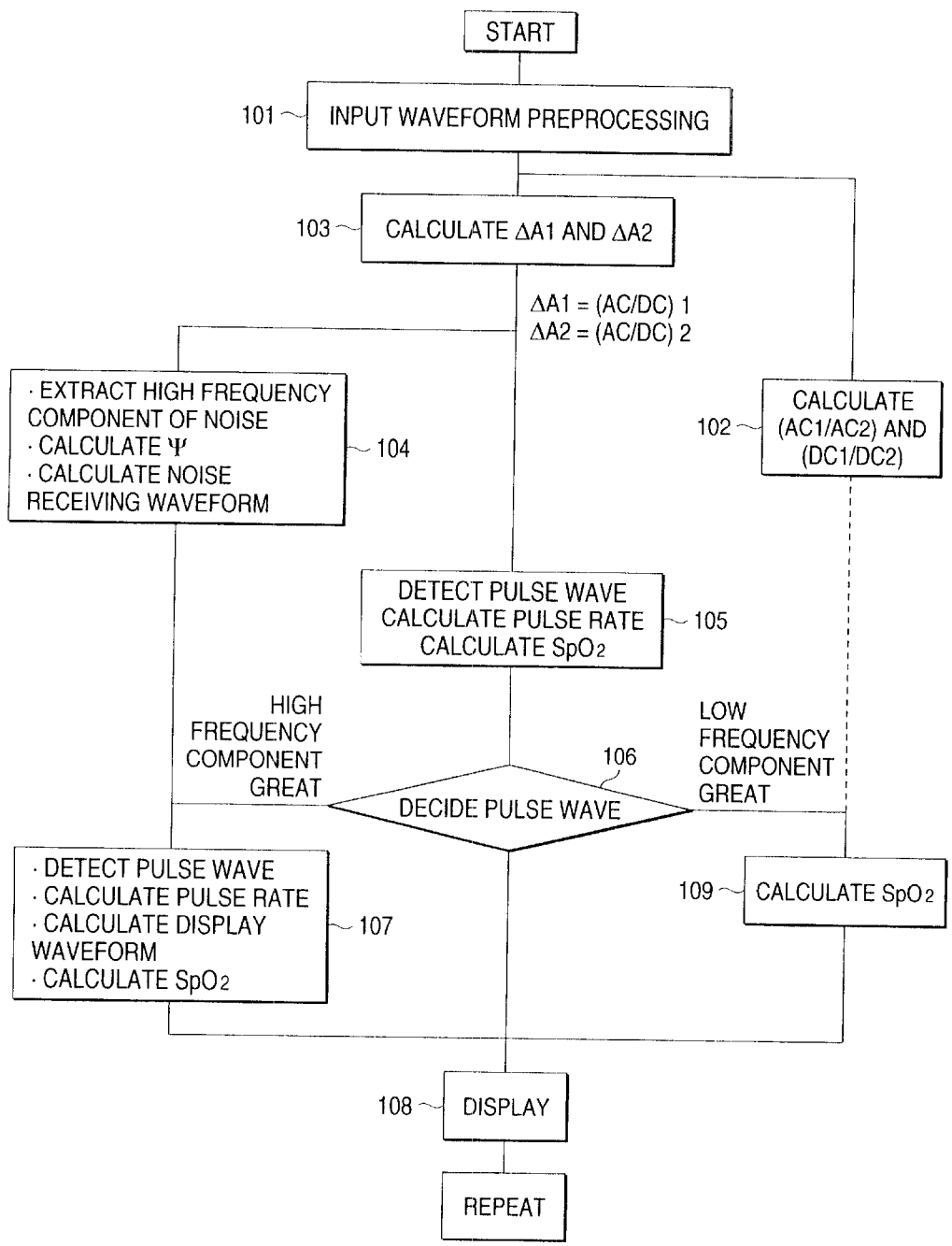
FIG. 2 is a flow chart for explaining the operation of the device shown in FIG. 1.

Then, an oxygen saturation is calculated from the corrected Φ (step 206) and the oxygen saturation thus obtained is displayed through the display unit 11 (step 108 in FIG. 2).

According to the present device described above, the processing is carried out depending on the noise condition.

Therefore, the measurement can be executed with high precision. Moreover, the pulse rate is detected and the signal having no noise is also displayed. Therefore, the state of a patient can be grasped more accurately.

In the above description, the lights having two wavelengths are used and the oxygen saturation is taken as an example of information about the light absorption material in blood. If lights having two or more wavelengths are used, concentrations of MetHb, COHb and 02Hb etc and a dye dilution curve can be obtained as other information about the light absorption material in blood in the same manner.

While the probe 1 serves to detect the transmitted light in the above example, it may detect the reflected light of the living tissue. Similarly, if a light-receiving signal is processed, the same function and effect can be obtained.

In the above example, the processing of the decision step 106 is carried out after the steps 104 and 105. After the measured values $\Delta A1$ and $\Delta A2$ are exactly used to calculate a pulse rate and an oxygen saturation and the high frequency component of a noise is extracted, the noise condition is decided. The decision step may be carried out before these steps. Furthermore, the decision step may be carried out before the steps 102 and 103. If the decision step 106 is thus carried out earlier, only a processing corresponding to the result of the decision can be executed. Thus, the processing can be simplified.

According to the invention, it is possible to remove a noise and to accurately obtain information about a light absorption material in blood in a signal processing based on an intensity of a transmitted light or a reflected light for a living tissue.

What is claimed is:

1. A device for measuring a light absorption material in blood, comprising:

light emitting means for emitting light, having a plurality of different wavelengths, onto a living tissue;

light receiving means for receiving light outputted from the light emitting means and transmitted through or reflected from the living tissue, the light receiving means outputting a signal corresponding to an intensity of the light transmitted through or reflected from the living tissue;

D.C./A.C. detecting means for obtaining a D.C. component and an A.C. component of a signal corresponding to each wavelength that is output from the light receiving means, respectively;

A.C. to D.C. ratio detecting means for obtaining an A.C. to D.C. ratio signal, which is a ratio of the A.C. component to the D.C. component for each wavelength calculated by the D.C./A.C. detecting means;

component extracting means for extracting a component from the A.C. to D.C. ratio signal having a predetermined frequency value, or a higher frequency value, for each wavelength which is obtained by the A.C. to D.C. ratio detecting means;

extracted component ratio detecting means for obtaining a ratio of extracted component signals for corresponding different wavelengths outputted from the light receiving means, which is extracted by the component extracting means; and information detecting means for detecting information about a light absorption material in blood, based on the ratio detected by the extracted component ratio detecting means.

2. The device for measuring the light absorption material in blood according to claim 1, wherein the information detecting means detects the information about the light absorption material in blood based on a predetermined relationship among the ratio detected by the extracted component ratio detecting means and the A.C. to D.C. ratio signal detected by the A.C. to D.C. ratio detecting means, wherein an ideal signal is provided when the A.C. to D.C. ratio signal has no noise component.

3. The device for measuring a light absorption material in blood according to claim 2, further comprising:

pulse rate detecting means for detecting a pulse rate based on the ideal signal.

4. The device for measuring a light absorption material in blood according to claim 2, further comprising:

display means for displaying a waveform of the ideal signal.

5. The device for measuring the light absorption material in blood according to the claim 1, wherein said predetermined frequency value is substantially a pulsation frequency value of living tissue.

6. The device for measuring a light absorption material in blood according to claim 1, wherein the information about the light absorption material in blood is an oxygen saturation.

7. The device for measuring a light absorption material in blood according to claim 1, wherein two wavelengths are used as the different wavelengths.

8. A device for measuring a light absorption material in blood, comprising:

light emitting means for emitting light, having a plurality of different wavelengths, onto a living tissue;

light receiving means for receiving light outputted from the light emitting means and transmitted through or reflected from the living tissue, the light receiving means outputting a signal corresponding to an intensity of the light transmitted through or reflected from the living tissue;

D.C./A.C. detecting means for obtaining a D.C. component and an A.C. component of a signal corresponding to each wavelength that is output from the light receiving means;

A.C. to D.C. ratio detecting means for obtaining an A.C. to D.C. ratio signal, which is a ratio of the A.C. component to the D.C. component for each wavelength calculated by the D.C./A.C. detecting means;

noise condition deciding means for deciding at least whether a noise component included in the A.C. to D.C. ratio signal, around a predetermined frequency value or a higher frequency value, is large; said noise condition detecting means comprising:

signal processing means for processing the A.C. to D.C. ratio signal for each wavelength which is obtained by the A.C. to D.C. ratio detecting means to detect information about a light absorption material in blood, said signal processing means comprising:

component extracting means for extracting a component from the A.C. to D.C. ratio signal having said predetermined frequency value or a higher frequency value for each wavelength which is obtained by the A.C. to D.C. ratio detecting means if the noise component for said predetermined frequency value or a higher frequency value, is large;

extracted component ratio detecting means for obtaining a ratio of extracted component signals for corresponding different wavelengths outputted from the light receiving means, which is extracted by the component extracting means; and information detecting means for detecting information about a light absorption material in blood, based on the ratio detected by the extracted component ratio detecting means.

9. The device for measuring the light absorption material in blood according to claim 8, wherein the information detecting means detects the information about the light absorption material in blood based on a predetermined relationship among the ratio detected by the extracted component ratio detecting means and the A.C. to D.C. ratio signal detected by the A.C. to D.C. ratio detecting means, wherein an ideal signal is provided when the A.C. to D.C. ratio signal has no noise component.

10. The device for measuring a light absorption material in blood according to claim 9, further comprising:

pulse rate detecting means for detecting a pulse rate based on the ideal signal.

11. The device for measuring a light absorption material in blood according to claim 9, further comprising:

display means for displaying a wave form of the ideal signal.

12. The device for measuring a light absorption material in blood according to the claim 8, wherein said predetermined frequency value is substantially a pulsation frequency value of living tissue.

13. The device for measuring a light absorption material in blood according to claim 8, wherein the information about the light absorption material in blood is an oxygen saturation.

14. The device for measuring a light absorption material in blood according to claim 8, wherein two wavelengths are used as the different wavelengths.

* * * * *